US005648458A

United States Patent [19]

Cwirla et al.

[11] Patent Number: 5,648,458
[45] Date of Patent: Jul. 15, 1997

[54] PEPTIDES AND COMPOUNDS THAT BIND TO ELAM-1

[75] Inventors: Steven E. Cwirla, Palo Alto; Ronald W. Barrett, Sunnyvale; William J. Dower, Menlo Park; Christine L. Martens, Portola Valley, all of Calif.

[73] Assignee: Affymax Technologies N.V., Curacao, Netherlands Antilles

[21] Appl. No.: 390,156

[22] Filed: Feb. 16, 1995

Related U.S. Application Data

[63] Continuation of Ser. No. 57,295, May 5, 1993, abandoned, which is a continuation-in-part of Ser. No. 881,395, May 6, 1992, abandoned.

[51] Int. Cl.$^6$ .............................. A61K 38/00; C07K 7/08; C07K 14/00
[52] U.S. Cl. .............................. 530/324; 530/327
[58] Field of Search .............................. 530/327; 514/12, 514/14

[56] References Cited

U.S. PATENT DOCUMENTS

| | | |
|---|---|---|
| 4,680,265 | 7/1987 | Birmingham et al. . |
| 5,010,175 | 4/1991 | Rutter et al. . |
| 5,053,392 | 10/1991 | Klein et al. . |
| 5,075,222 | 12/1991 | Hannum et al. ......................... 435/69.1 |
| 5,081,034 | 1/1992 | Bevilacqua et al. ............... 435/252.33 |
| 5,143,854 | 9/1992 | Pirrung et al. ........................... 436/518 |
| 5,166,133 | 11/1992 | Houston et al. . |
| 5,208,253 | 5/1993 | Boschelli . |
| 5,258,289 | 11/1993 | Davis et al. . |
| 5,268,364 | 12/1993 | Kojima et al. . |
| 5,324,591 | 6/1994 | Georger, Jr. et al. . |

FOREIGN PATENT DOCUMENTS

| | | |
|---|---|---|
| 505 749 | 9/1992 | European Pat. Off. . |
| WO90/05539 | 5/1990 | WIPO . |
| WO90/13300 | 11/1990 | WIPO . |
| WO90/15070 | 12/1990 | WIPO . |
| WO91/05058 | 4/1991 | WIPO . |
| WO91/16900 | 11/1991 | WIPO . |
| WO91/19502 | 12/1991 | WIPO . |
| WO91/19818 | 12/1991 | WIPO . |
| WO92/00995 | 1/1992 | WIPO . |
| WO92/02527 | 2/1992 | WIPO . |
| WO92/01718 | 2/1992 | WIPO . |
| WO92/07572 | 5/1992 | WIPO . |
| WO92/08488 | 5/1992 | WIPO . |
| WO92/09293 | 6/1992 | WIPO . |
| WO92/12729 | 8/1992 | WIPO . |
| WO92/18610 | 10/1992 | WIPO . |
| WO92/19646 | 11/1992 | WIPO . |
| WO92/19735 | 11/1992 | WIPO . |
| WO92/20708 | 11/1992 | WIPO . |
| WO93/07268 | 4/1993 | WIPO . |
| WO93/06865 | 4/1993 | WIPO . |
| WO93/24526 | 12/1993 | WIPO . |
| 9305070 | 2/1994 | WIPO . |
| WO94/05269 | 3/1994 | WIPO . |
| WO94/05310 | 3/1994 | WIPO . |
| WO94/11498 | 5/1994 | WIPO . |
| WO92/12994 | 8/1994 | WIPO . |
| WO94/17193 | 8/1994 | WIPO . |

OTHER PUBLICATIONS

Roemer et al, PNAS, vol. 88, pp. 11295–11299. 1991.
Edgington, Biotechnology, vol. 10, pp. 383–389, 1992.
Barrett, et al, *Analytical Biochemistry*, 204, 357–364 pp. (1992).
Cwirla, et al, *Proc. Natl. Acad. Sci*, 87, 6378–6382 (1990).
Bochelli, J., "3–Alkoxybenzo[b]thiophene–2–carboxamides as Inhibitors of Neutrophil–endothelial Cell Adhesion", *Medical Chem.*, 37(6).
Cho, Charles, Y. et al., "An Unnatural Biopolymer", *Science*, vol. 261, Sep. 3, 1993, pp. 1303–1305.
Geng, Jian–Guo et al., "Rapid Neutrophil Adhesion to Activated Endothelium Mediated by GMP–140", *Nature*, vol. 343, Feb. 22, 1990, pp. 757–760.
Hession C. et al., "Endothelial Leukocyte Adhesion Molecule 1: Direct Expression Cloning and Functional Interactions", *Proc. Nat. Acad. Sci. USA*, vol. 87 (Cell Biology), Mar. 1990, pp. 1673–1677.
Johnston, Geoffrey I. et al., "Cloning of GMP–140, a Granule Membrane Protein of Platelets and Endothelium: Sequence Similarity to Proteins Involved in Cell Adhesion and Inflammation", *Cell*, pp. 1034–1044. (1990).
Oliphant, Arnold R. et al., "Defining the Sequence Specificity of DNA–Binding Proteins by Selecting Binding Sites from Random–Sequence Oligonucleotides: Analysis of Yeast GCN4 Protein", *Molecular and Cellular Biology*, vol. 9, No. 7, Jul. 1989, pp. 2944–2949.
Spertini, Olivier et al., "Regulation of Leukocyte Migration by Activation of the Leukocyte Adhesion Molecule–1 (LAM–1 Selectin)", *Nature*, vol. 349, Feb. 21, 1991, pp. 691–693.
Springer, Timothy A., "Adhesion Receptors of the Immune System", Review Article, *Nature*, vol. 346, Aug. 2, 1990, pp. 425–434.
Bender et al, "Chapter 20: Pharmacological Modulation of Interleukin–1," *Ann. Rep. Med. Chem.*, vol. 25:185–193.
Bevilacqua et al, "Selectins: A Family of Adhesion Receptors," *Cell*, Oct. 18, 1991, vol. 67:233.
Ezzell, "Sticky Situations: Picking Apart the Molecules that Glue Cells Together," *Science News*, Jun. 13, 1992, vol. 141:392–395.
Goelz et al, "ELFT: A Gene that Directs the Expression of an ELAM–1 Ligand," *Cell*, 1990, vol. 63:1349–1356.

(List continued on next page.)

*Primary Examiner*—Cecilia Tsang
*Assistant Examiner*—S. G. Marshall
*Attorney, Agent, or Firm*—Kevin R. Kaster; Vern A. Norviel; Lauren L. Stevens

[57] ABSTRACT

The peptide HITWDQLWNVMN (SEQ ID NO: 4) and related peptides and peptidomimetics bind to endothelial leukocyte adhesion molecule 1 and block the binding of leukocytes to this important receptor and so can be used to ameliorate the detrimental effects of certain disease conditions.

14 Claims, 5 Drawing Sheets

OTHER PUBLICATIONS

Parekh, "Oligosaccharides as Specific Ligands for the LECAMs," *Tech. Bull.* 11, 1991, Oxford GlycoSystems Ltd.

Phillips et al, "ELAM-1 Mediates Cell Adhesion by Recognition of a Carbohydrate Ligand, Sialyl-Lex," *Science*, Nov. 23, 1990, vol. 25:1130-1135.

Polley et al, "CD62 and Endothelial Cell-Leukocyte Adhesion Molecule 1 (ELAM-1) Recognize the Same Carbohydrate Ligand, Sialyl-Lewis x," *PNAS, USA*, Jul. 1991, vol. 88:6224-6228.

Rice et al, "An Inducible Endothelial Cell Surface Glycoprotein Mediates Melanoma Adhesion," *Science*, Dec. 8, 1989, vol. 246:1303-1306.

Tiemeyer et al, "Carbohydrate Ligands for Endothelial-Leukocyte Adhesion Molecule 1," *PNAS, USA*, Feb. 1991, vol. 88:1138-1143.

Tyrrell et al, "Structural Requirements for the Carbohydrate Ligand of E-Selectin," *PNAS USA*, Nov. 1991, vol. 88:10372-10376.

Paulson, Selectin/carbohydrate-mediated adhesion of leukocytes, Adhesion: It's Role in Inflammatory Disease, Chapter 2, pp. 19-42 (1992).

Picker et al., ELAM-1 is an adhesion molecule for skin-homing T cells (1991) Nature 349:796-799.

Schimizu et al., Activation-independent binding of human memory T cells to adhesion molecule ELAM-1 (1991) Nature 349:799-802.

Collins et al., Structure and chromosomal location of the gene for endothelial-leukocyte adhesion molecule 1 (1991) J. Biol. Chem. 266:2466-2473.

Figure 2a
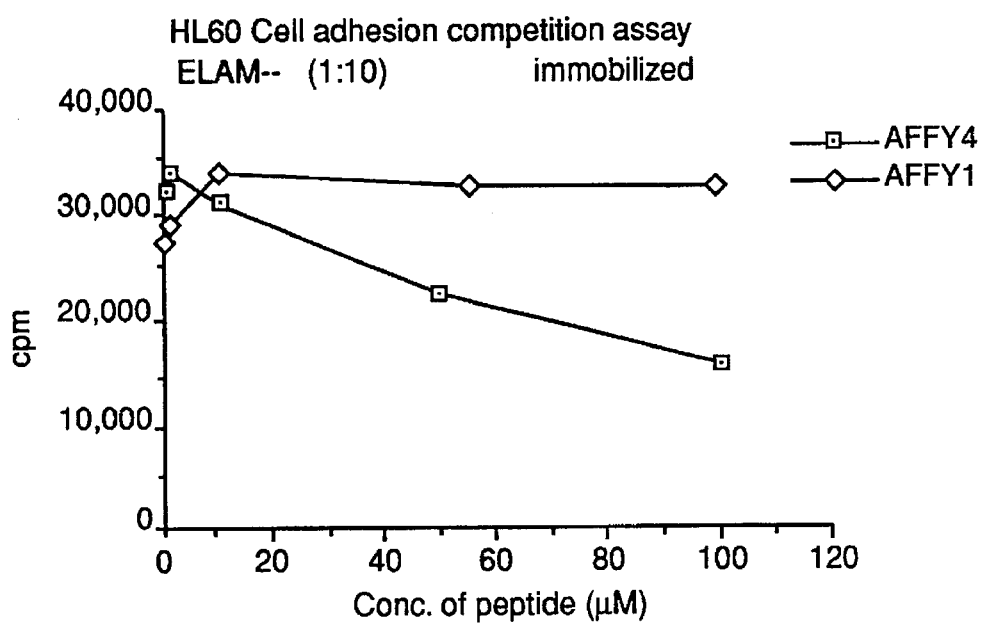
Figure 2b
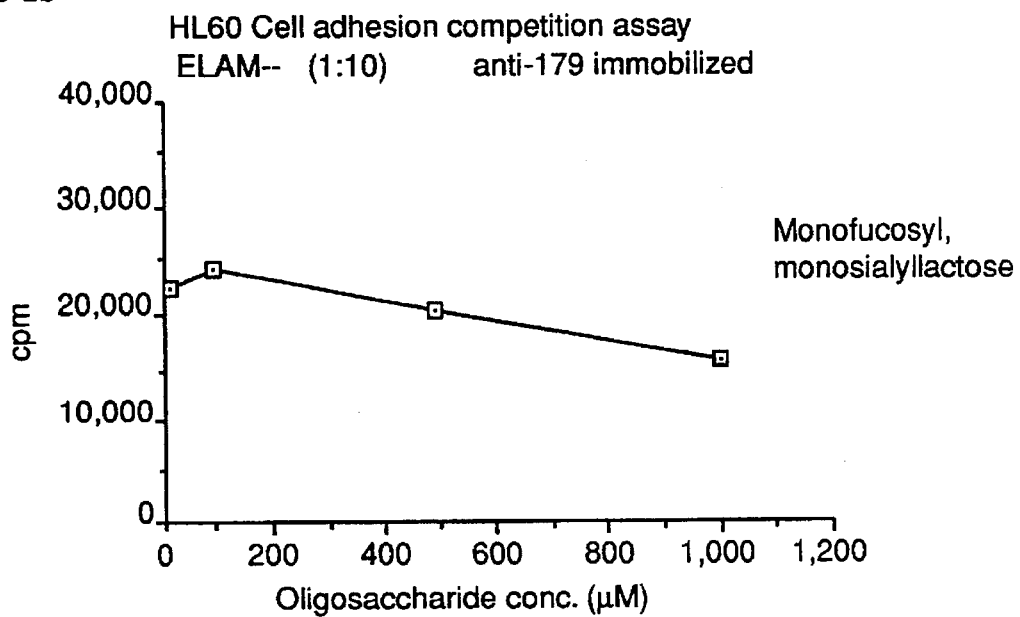
Figures 2a & 2b

Binding assay with lacI fusion peptide

Competition assay

| Peptide Sequence | IC50 |
| --- | --- |
| DITWDQLWDLMK | 3 |
| DGDITWDQLWDLMK | 4 |
| DYTWFELWDMMQ | 6 |
| DITWDELWKIMN | 7 |
| QITWAQLWNMMK | 12 |
| DYSWHDLWEMMS | 16 |
| DITWDQLWDLNleK | 23 |
| HITWDQLWRIMT | 28 |
| RNMSWLELWEHMK | 35 |
| DGDITWDQLWDLNleK | 42 |
| HVSWEQLWDIMN | 47 |
| DMTWHDLWTLMS | 50 |
| QITWDQLWDLNleK | 65 |
| AETWDQLWHVMNPAESQ | 65 |
| EITWDQLWEVMN | 82 |
| DITWAQLWNNleNleN | 425 |
| KKEDWLALWRIMSV | 435 |
| DISWDDLWIMMN | 400 |
| QITWDQLWDLMY | 400 |
| HRAEWLALWEQMS | 455 |
| KRKQWIELWNIMS | 2μM |
| D-DITWDQLWDLMK | 25 |
| Dd-ITWDQLWDLMK | 27 |
| DId-TWDQLWDLMK | 2700 |
| DITWd-DQLWDLMK | 34 |
| DITWDQLWDd-LMK | 33000 |
| DITWDQLWDLMd-K | 1000 |
| DITWDQLWDLMK-CONH$_2$ | 22 |
| ITWDQLWDLMK | 11 |
| TWDQLWDLMK | 12μM |
| DITWDQLWDLM | 867 |
| DITWDQLWDL | 55μM |

IC50 is in nanomolar unless otherwise noted

Figure 4

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Trp Xaa Xaa Leu Trp Xaa Xaa Met
1               5

( 2 ) INFORMATION FOR SEQ ID NO:2:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Ile Thr Trp Asp Gln Leu Trp Asp Leu Met Lys
1               5                   10

( 2 ) INFORMATION FOR SEQ ID NO:3:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:3:

Asp Ile Thr Trp Asp Gln Leu Trp Asp Leu Met Lys
1               5                   10

( 2 ) INFORMATION FOR SEQ ID NO:4:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:4:

His Ile Thr Trp Asp Gln Leu Trp Asn Val Met Asn
1               5                       10

( 2 ) INFORMATION FOR SEQ ID NO:5:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

His Ile Thr Trp Asp Gln Xaa Xaa Xaa Xaa Xaa Xaa
1               5                       10

( 2 ) INFORMATION FOR SEQ ID NO:6:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

Xaa Xaa Thr Trp Asp Gln Leu Trp Xaa Xaa Xaa Xaa
1               5                       10

( 2 ) INFORMATION FOR SEQ ID NO:7:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

Xaa Xaa Xaa Xaa Asp Gln Leu Trp Asn Val Xaa Xaa
1               5                       10

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

Xaa Xaa Xaa Xaa Xaa Xaa Leu Trp Asn Val Met Asn
1               5                       10

( 2 ) INFORMATION FOR SEQ ID NO:9:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Xaa Xaa Xaa Xaa His Ile Thr Trp Asp Gln Leu Trp Asn Val Met Asn
1               5                   10                  15
Xaa Xaa Xaa Xaa
            20
```

( 2 ) INFORMATION FOR SEQ ID NO:10:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Gln Ile Thr Trp Ala Gln Leu Trp Asn Met Met Lys
1               5                   10
```

( 2 ) INFORMATION FOR SEQ ID NO:11:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Xaa Xaa Xaa Trp Xaa Xaa Leu Trp Xaa Xaa Met Xaa
1               5                   10
```

( 2 ) INFORMATION FOR SEQ ID NO:12:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Xaa Xaa Xaa Xaa Trp Xaa Xaa Leu Trp Xaa Xaa Met Xaa Xaa Xaa Xaa
1               5                   10                  15
Xaa Xaa
```

( 2 ) INFORMATION FOR SEQ ID NO:13:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Glu Leu Thr Trp Asp Gln Leu Trp Val Leu Met Ser
1               5                   10
```

( 2 ) INFORMATION FOR SEQ ID NO:14:

( i ) SEQUENCE CHARACTERISTICS:
        ( A ) LENGTH: 12 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:14:

```
Glu  Val  Thr  Trp  Asp  Gln  Leu  Trp  Val  Met  Met  Gln
1                   5                        10
```

(2) INFORMATION FOR SEQ ID NO:15:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:15:

```
Glu  Met  Ser  Trp  Leu  Glu  Leu  Trp  Asn  Val  Met  Asn
1                   5                        10
```

(2) INFORMATION FOR SEQ ID NO:16:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:16:

```
Glu  Leu  Ser  Trp  Asp  Gln  Leu  Trp  Asn  Val  Met  Asn
1                   5                        10
```

(2) INFORMATION FOR SEQ ID NO:17:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:17:

```
Glu  Met  Thr  Trp  Thr  Glu  Leu  Trp  Asn  Val  Met  Asn
1                   5                        10
```

(2) INFORMATION FOR SEQ ID NO:18:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:18:

```
Glu  Met  Thr  Trp  Leu  Gly  Leu  Trp  Asn  Val  Met  Asn
1                   5                        10
```

(2) INFORMATION FOR SEQ ID NO:19:

(i) SEQUENCE CHARACTERISTICS:
(A) LENGTH: 12 amino acids
(B) TYPE: amino acid (C) STRANDEDNESS: single
(D) TOPOLOGY: linear (i i) MOLECULE TYPE: peptide (x i) SEQUENCE DESCRIPTION: SEQ ID NO:19:

Glu Ile Thr Trp Asp Gln Leu Trp Glu Val Met Asn
1               5                   10

(2) INFORMATION FOR SEQ ID NO:20:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:20:

Asp Ile Ser Trp Asp Gln Leu Trp Asn Val Met Asn
1               5                   10

(2) INFORMATION FOR SEQ ID NO:21:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:21:

Glu Met Thr Trp Asp Gln Leu Trp Asn Val Met Asn
1               5                   10

(2) INFORMATION FOR SEQ ID NO:22:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:22:

Asp Ile Thr Trp Asn Met Leu Trp Asn Met Met Gln
1               5                   10

(2) INFORMATION FOR SEQ ID NO:23:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:23:

Asp Ile Thr Trp His Gln Leu Trp Asn Leu Met Asn
1               5                   10

(2) INFORMATION FOR SEQ ID NO:24:

(i) SEQUENCE CHARACTERISTICS:
    (A) LENGTH: 12 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:24:

```
Asp Ile Thr Trp Glu Gln Leu Trp Asn Met Met Asn
1               5                   10
```

(2) INFORMATION FOR SEQ ID NO:25:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:25:

```
Asp Ile Thr Trp His Gln Leu Trp Asn Leu Met Asn
1               5                   10
```

(2) INFORMATION FOR SEQ ID NO:26:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:26:

```
Asp Ile Thr Trp Glu Gln Leu Trp Asn Leu Met Asn
1               5                   10
```

(2) INFORMATION FOR SEQ ID NO:27:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:27:

```
His Ile Ser Trp His Glu Leu Trp Asn Leu Met Gln
1               5                   10
```

(2) INFORMATION FOR SEQ ID NO:28:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:28:

```
His Ile Thr Trp Asp Gln Leu Trp Asp Leu Met Gln
1               5                   10
```

(2) INFORMATION FOR SEQ ID NO:29:

(i) SEQUENCE CHARACTERISTICS:
(A) LENGTH: 12 amino acids
(B) TYPE: amino acid (C) STRANDEDNESS: single
(D) TOPOLOGY: linear (ii) MOLECULE TYPE: peptide (xi) SEQUENCE DESCRIPTION: SEQ ID NO:29:

Gln Ile Thr Trp Asp Gln Leu Trp Asn Met Met Ile
1               5                   10

(2) INFORMATION FOR SEQ ID NO:30:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:30:

Tyr Ile Thr Trp Glu Gln Leu Trp Asn Met Met Asn
1               5                   10

(2) INFORMATION FOR SEQ ID NO:31:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:31:

His Ile Thr Trp Asp Gln Leu Trp Glu Ile Met Ser
1               5                   10

(2) INFORMATION FOR SEQ ID NO:32:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:32:

His Ile Thr Trp Asp Gln Leu Trp Ser Leu Met Ser
1               5                   10

(2) INFORMATION FOR SEQ ID NO:33:

(i) SEQUENCE CHARACTERISTICS:
    (A) LENGTH: 12 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:33:

His Ile Thr Trp Asp Gln Leu Trp Asp Leu Met Gln
1               5                   10

(2) INFORMATION FOR SEQ ID NO:34:

(i) SEQUENCE CHARACTERISTICS:
    (A) LENGTH: 12 amino acids
    (B) TYPE: amino acid (C) STRANDEDNESS: single
(D) TOPOLOGY: linear (ii) MOLECULE TYPE: peptide (xi) SEQUENCE DESCRIPTION: SEQ ID NO:34:

His Ile Thr Trp Asp Gln Leu Trp Leu Leu Met Ala
1               5                   10

(2) INFORMATION FOR SEQ ID NO:35:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:35:

Gly Ser Asp Ser His Ile Thr Trp Asp Glu Leu Trp Asn Leu Met Asn
1               5                   10                  15

Pro Val Leu Ala
            20

(2) INFORMATION FOR SEQ ID NO:36:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:36:

Glu Thr Asp Asp His Ile Thr Trp Asp Gln Leu Trp Arg Ile Met Thr
1               5                   10                  15

Ala Thr Met Ala
            20

(2) INFORMATION FOR SEQ ID NO:37:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:37:

Gly Phe Gly Glu Ala Ile Thr Trp Asp Gln Leu Trp Asp Met Met Asn
1               5                   10                  15

Gly Glu Asp Ala
            20

(2) INFORMATION FOR SEQ ID NO:38:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:38:

```
Gly Gln Thr Gly Leu Ile Thr Trp Asp Met Leu Trp Asn Leu Met Asn
1               5                   10                  15

Pro Val Gly Glu
            20
```

( 2 ) INFORMATION FOR SEQ ID NO:39:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:39:

```
Glu Tyr Gly Arg His Ile Thr Trp Asp Gln Leu Trp Gln Leu Met Gln
1               5                   10                  15

Ser Ala Thr Ala
            20
```

( 2 ) INFORMATION FOR SEQ ID NO:40:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:40:

```
Glu Ser Ala Ser His Ile Thr Trp Gly Gln Leu Trp Asp Leu Met Asn
1               5                   10                  15

Ala Ser Glu Val
            20
```

( 2 ) INFORMATION FOR SEQ ID NO:41:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:41:

```
Ala Gly Ala Ser His Ile Thr Trp Ala Gln Leu Trp Asn Met Met Asn
1               5                   10                  15

Gly Asn Glu Gly
            20
```

( 2 ) INFORMATION FOR SEQ ID NO:42:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:42:

```
Tyr Gly Asn Ser Asn Ile Thr Trp Asp Gln Leu Trp Ser Ile Met Asn
1               5                   10                  15

Arg Gln Thr Thr
```

20

(2) INFORMATION FOR SEQ ID NO:43:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Glu  Ser  Ala  Ser  His  Ile  Thr  Trp  Gly  Gln  Leu  Trp  Asp  Leu  Met  Asn
  1              5                       10                       15
Ala  Ser  Glu  Val
              20
```

(2) INFORMATION FOR SEQ ID NO:44:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:44:

```
Gly  Phe  Gly  Glu  Ala  Ile  Thr  Trp  Asp  Gln  Leu  Trp  Asp  Met  Met  Asn
  1              5                       10                       15
Gly  Glu  Asp  Ala
              20
```

(2) INFORMATION FOR SEQ ID NO:45:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:45:

```
Glu  Met  Thr  Trp  Ala  Glu  Leu  Trp  Thr  Leu  Met  Glu
  1              5                       10
```

(2) INFORMATION FOR SEQ ID NO:46:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:46:

```
Ala  Ile  Thr  Trp  Asp  Gln  Leu  Trp  Leu  Leu  Met  Ser
  1              5                       10
```

(2) INFORMATION FOR SEQ ID NO:47:

(i) SEQUENCE CHARACTERISTICS:
        (A) LENGTH: 12 amino acids
        (B) TYPE: amino acid
        (C) STRANDEDNESS: single
        (D) TOPOLOGY: linear ( i i ) MOLECULE TYPE: peptide ( x i ) SEQUENCE DESCRIPTION: SEQ ID NO:47:

Asp Val Thr Trp Asp Gln Leu Trp Glu Leu Met Thr
1               5                   10

( 2 ) INFORMATION FOR SEQ ID NO:48:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

Asn Leu Thr Trp Asp Gln Leu Trp Val Leu Met Ser
1               5                   10

( 2 ) INFORMATION FOR SEQ ID NO:49:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

Thr Ile Thr Trp Asp Gln Leu Trp Gln Met Met Ser
1               5                   10

( 2 ) INFORMATION FOR SEQ ID NO:50:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

Glu Met Thr Trp Gln Glu Leu Trp Asn Val Met Asn
1               5                   10

( 2 ) INFORMATION FOR SEQ ID NO:51:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

Asp Met Thr Trp Ser Gln Leu Trp Asn Val Met Asn
1               5                   10

( 2 ) INFORMATION FOR SEQ ID NO:52:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear (i i) MOLECULE TYPE: peptide (x i) SEQUENCE DESCRIPTION: SEQ ID NO:52:

Gln Ile Thr Trp Met Glu Leu Trp Asn Leu Met Asn
1               5                   10

(2) INFORMATION FOR SEQ ID NO:53:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:53:

Glu Ile Thr Trp Asp Gln Leu Trp Asp Val Met Asn
1               5                   10

(2) INFORMATION FOR SEQ ID NO:54:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:54:

Gln Ile Thr Trp Asp Gln Leu Trp Asp Leu Met Lys
1               5                   10

(2) INFORMATION FOR SEQ ID NO:55:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:55:

Asp Ile Thr Trp Asp Gln Leu Trp Asn Met Met Asp
1               5                   10

(2) INFORMATION FOR SEQ ID NO:56:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:56:

Asp Ile Ser Trp Asp Asp Leu Trp Ile Met Met Asn
1               5                   10

(2) INFORMATION FOR SEQ ID NO:57:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:57:

```
Glu Ile Ser Trp Glu Gln Leu Trp Thr Met Met Asn
1               5                   10
```

(2) INFORMATION FOR SEQ ID NO:58:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:58:

```
Glu Ile Thr Trp Asp Gln Leu Trp Thr Leu Met Thr
1               5                   10
```

(2) INFORMATION FOR SEQ ID NO:59:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:59:

```
Asp Met Thr Trp Asp Gln Leu Trp Ile Val Met Asn
1               5                   10
```

(2) INFORMATION FOR SEQ ID NO:60:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:60:

```
Gln Ile Thr Trp Tyr Gln Leu Trp Asn Met Met Asn
1               5                   10
```

(2) INFORMATION FOR SEQ ID NO:61:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:61:

```
Tyr Ile Thr Trp Glu Gln Leu Trp Thr Met Met Asn
1               5                   10
```

(2) INFORMATION FOR SEQ ID NO:62:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (x i) SEQUENCE DESCRIPTION: SEQ ID NO:62:

Gln Ile Thr Trp Asp Gln Leu Trp Asp Leu Met Tyr
1               5                   10

(2) INFORMATION FOR SEQ ID NO:63:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:63:

His Ile Thr Trp Asp Gln Leu Trp Asp Ile Met Ser
1               5                   10

(2) INFORMATION FOR SEQ ID NO:64:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:64:

His Ile Thr Trp Asp Gln Leu Trp Ala Leu Met Thr
1               5                   10

(2) INFORMATION FOR SEQ ID NO:65:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:65:

His Ile Thr Trp Asp Gln Leu Trp Leu Met Met Ser
1               5                   10

(2) INFORMATION FOR SEQ ID NO:66:

(i) SEQUENCE CHARACTERISTICS:
    (A) LENGTH: 12 amino acids
    (B) TYPE: amino acid
    (C) STRANDEDNESS: single
    (D) TOPOLOGY: linear (i i) MOLECULE TYPE: peptide (x i) SEQUENCE DESCRIPTION: SEQ ID NO:66:

His Ile Thr Trp Asp Gln Leu Trp Trp Ile Met Ala
1               5                   10

(2) INFORMATION FOR SEQ ID NO:67:

(i) SEQUENCE CHARACTERISTICS:
    (A) LENGTH: 12 amino acids
    (B) TYPE: amino acid
    (C) STRANDEDNESS: single
    (D) TOPOLOGY: linear ( i i ) MOLECULE TYPE: peptide ( x i ) SEQUENCE DESCRIPTION: SEQ ID NO:67:

```
His Ile Thr Trp Asp Gln Leu Trp Met Leu Met Ala
1               5                  10
```

( 2 ) INFORMATION FOR SEQ ID NO:68:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:68:

```
Asn Trp Leu Asp Asp Ile Thr Trp Asp Glu Leu Trp Lys Ile Met Asn
1               5                   10                  15

Pro Ser Thr Ala
                20
```

( 2 ) INFORMATION FOR SEQ ID NO:69:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:69:

```
Trp Thr Asp Thr His Ile Thr Trp Asp Gln Leu Trp His Phe Met Asn
1               5                   10                  15

Met Gly Glu Gln
                20
```

( 2 ) INFORMATION FOR SEQ ID NO:70:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:70:

```
Asn Val Ala Glu Gln Ile Thr Trp Asp Gln Leu Trp Asn Leu Met Ser
1               5                   10                  15

Val Gly Ser Ser
                20
```

( 2 ) INFORMATION FOR SEQ ID NO:71:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:71:

```
Gly Thr Gly Asp His Ile Thr Trp Asp Gln Leu Trp Asn Leu Met Ile
1               5                   10                  15
```

Asn Glu Lys Gly
            20

( 2 ) INFORMATION FOR SEQ ID NO:72:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:72:

Met Asn Asn Trp His Val Ser Trp Glu Gln Leu Trp Asp Ile Met Asn
1               5                   10                  15

Gly Pro Pro Asn
            20

( 2 ) INFORMATION FOR SEQ ID NO:73:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:73:

Tyr Trp Arg Gly Asn Ile Thr Trp Asp Gln Leu Trp Asn Ile Met Asn
1               5                   10                  15

Ser Glu Tyr Ser
            20

( 2 ) INFORMATION FOR SEQ ID NO:74:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:74:

Gly Ser Trp Ala His Ile Thr Trp Asp Gln Leu Trp Asn Leu Met Asn
1               5                   10                  15

Met Gly Thr Gln
            20

( 2 ) INFORMATION FOR SEQ ID NO:75:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:75:

Ala His Leu Pro His Ile Ser Trp Asp Thr Leu Trp His Ile Met Asn
1               5                   10                  15

Lys Gly Glu Lys
            20

( 2 ) INFORMATION FOR SEQ ID NO:76:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:76:

```
Asp Tyr Thr Trp Phe Glu Leu Trp Asp Met Met Gln
1               5                   10
```

( 2 ) INFORMATION FOR SEQ ID NO:77:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:77:

```
Asp Tyr Ser Trp His Asp Leu Trp Glu Met Met Ser
1               5                   10
```

( 2 ) INFORMATION FOR SEQ ID NO:78:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:78:

```
Glu Ile Ser Trp Leu Gly Leu Trp Asp Ile Met Asn
1               5                   10
```

( 2 ) INFORMATION FOR SEQ ID NO:79:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:79:

```
Arg Gly Val Met Gly Gly Leu Trp Ser Met Thr Trp
1               5                   10
```

( 2 ) INFORMATION FOR SEQ ID NO:80:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:80:

```
Ala Glu Trp Thr Trp Asp Gln Leu Trp His Val Met Asn Pro Ala Glu
1               5                   10                  15
```

Ser Gln (2) INFORMATION FOR SEQ ID NO:81:

(i) SEQUENCE CHARACTERISTICS:
        (A) LENGTH: 18 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:81:

```
Ser Gln Val Thr Trp Asn Asp Leu Trp Ser Val Met Asn Pro Glu Val
1               5                   10                  15
Val Asn
```

(2) INFORMATION FOR SEQ ID NO:82:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:82:

```
Tyr Lys Lys Glu Trp Leu Glu Leu Trp His Gln Met Gln Ala
1               5                   10
```

(2) INFORMATION FOR SEQ ID NO:83:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:83:

```
Lys Glu Gln Gln Trp Arg Asn Leu Trp Lys Met Met Ser
1               5                   10
```

(2) INFORMATION FOR SEQ ID NO:84:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:84:

```
Arg Asn Met Ser Trp Leu Glu Leu Trp Glu His Met Lys
1               5                   10
```

(2) INFORMATION FOR SEQ ID NO:85:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:85:

```
Lys  Arg  Lys  Gln  Trp  Ile  Glu  Leu  Trp  Asn  Ile  Met  Ser
1              5                        10
```

( 2 ) INFORMATION FOR SEQ ID NO:86:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:86:

```
Asp  Ile  Ser  Trp  Arg  Gln  Leu  Trp  Asp  Ile  Met  Asn
1              5                        10
```

( 2 ) INFORMATION FOR SEQ ID NO:87:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

```
Asp  Met  Thr  Trp  His  Asp  Leu  Trp  Thr  Leu  Met  Ser
1              5                        10
```

( 2 ) INFORMATION FOR SEQ ID NO:88:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:88:

```
Glu  Met  Thr  Trp  Gln  Gln  Leu  Trp  Val  Val  Met  Gln
1              5                        10
```

( 2 ) INFORMATION FOR SEQ ID NO:89:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:89:

```
His  Arg  Ala  Glu  Trp  Leu  Ala  Leu  Trp  Glu  Gln  Met  Ser  Pro
1              5                        10
```

( 2 ) INFORMATION FOR SEQ ID NO:90:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:90:

```
        Arg   Ser   Leu   Ser   Trp   Leu   Gln   Leu   Trp   Asp   Gln   Met   Lys
        1                 5                             10
```

( 2 ) INFORMATION FOR SEQ ID NO:91:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:91:

```
        Lys   Lys   Glu   Asp   Trp   Leu   Ala   Leu   Trp   Arg   Ile   Met   Ser   Val   Pro   Asp
        1                 5                             10                              15
```

( 2 ) INFORMATION FOR SEQ ID NO:92:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:92:

```
        Gly   Arg   Pro   Thr   Trp   Asn   Glu   Leu   Trp   Asp   Met   Met   Gln   Ala   Pro
        1                 5                             10                              15
```

( 2 ) INFORMATION FOR SEQ ID NO:93:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:93:

```
        Lys   Thr   Ser   Glu   Trp   Asn   Asn   Leu   Trp   Lys   Leu   Met   Ser   Gln
        1                 5                             10
```

( 2 ) INFORMATION FOR SEQ ID NO:94:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:94:

```
        Asp   Gln   Ile   Thr   Trp   Ala   Gln   Leu   Trp   Asn   Met   Met   Lys   Gly   Gly   Thr
        1                 5                             10                              15

Val   Glu
```

( 2 ) INFORMATION FOR SEQ ID NO:95:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 8
        ( D ) OTHER INFORMATION: /note= "Xaa is norleucine"

( x i ) SEQUENCE DESCRIPTION: SEQ ID NO:95:

```
Trp  Xaa  Xaa  Leu  Trp  Xaa  Xaa  Xaa
1                  5
```

( 2 ) INFORMATION FOR SEQ ID NO:96:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

```
Asp  Gly  Asp  Ile  Thr  Trp  Asp  Gln  Leu  Trp  Asp  Leu  Met  Lys
1                   5                        10
```

( 2 ) INFORMATION FOR SEQ ID NO:97:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

```
Asp  Ile  Thr  Trp  Asp  Glu  Leu  Trp  Lys  Ile  Met  Asn
1                   5                        10
```

( 2 ) INFORMATION FOR SEQ ID NO:98:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 11
        ( D ) OTHER INFORMATION: /note= "Xaa is norleucine."

( x i ) SEQUENCE DESCRIPTION: SEQ ID NO:98:

```
Asp  Ile  Thr  Trp  Asp  Gln  Leu  Trp  Asp  Leu  Xaa  Lys
1                   5                        10
```

( 2 ) INFORMATION FOR SEQ ID NO:99:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:99:

```
His  Ile  Thr  Trp  Asp  Gln  Leu  Trp  Arg  Ile  Met  Thr
1                   5                        10
```

5,648,458

( 2 ) INFORMATION FOR SEQ ID NO:100:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 13
        ( D ) OTHER INFORMATION: /note= "Xaa is norleucine."

( x i ) SEQUENCE DESCRIPTION: SEQ ID NO:100:

```
Asp  Gly  Asp  Ile  Thr  Trp  Asp  Gln  Leu  Trp  Asp  Leu  Xaa  Lys
 1              5                        10
```

( 2 ) INFORMATION FOR SEQ ID NO:101:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:101:

```
His  Val  Ser  Trp  Glu  Gln  Leu  Trp  Asp  Ile  Met  Asn
 1              5                        10
```

( 2 ) INFORMATION FOR SEQ ID NO:102:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 11
        ( D ) OTHER INFORMATION: /note= "Xaa is norleucine."

( x i ) SEQUENCE DESCRIPTION: SEQ ID NO:102:

```
Gln  Ile  Thr  Trp  Asp  Gln  Leu  Trp  Asp  Leu  Xaa  Lys
 1              5                        10
```

( 2 ) INFORMATION FOR SEQ ID NO:103:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Region
        ( B ) LOCATION: 10
        ( D ) OTHER INFORMATION: /note= "Xaa is norleucine."

( i x ) FEATURE:
        ( A ) NAME/KEY: Region
        ( B ) LOCATION: 11
        ( D ) OTHER INFORMATION: /note= "Xaa is norleucine."

( x i ) SEQUENCE DESCRIPTION: SEQ ID NO:103:

```
    Asp  Ile  Thr  Trp  Ala  Gln  Leu  Trp  Asn  Xaa  Xaa  Asn
    1              5                        10
```

( 2 ) INFORMATION FOR SEQ ID NO:104:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:104:

```
    Lys  Lys  Glu  Asp  Trp  Leu  Ala  Leu  Trp  Arg  Ile  Met  Ser  Val
    1              5                        10
```

( 2 ) INFORMATION FOR SEQ ID NO:105:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:105:

```
    Asp  Ile  Ser  Trp  Asp  Asp  Leu  Trp  Ile  Met  Met  Asn
    1              5                        10
```

( 2 ) INFORMATION FOR SEQ ID NO:106:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:106:

```
    His  Arg  Ala  Glu  Trp  Leu  Ala  Leu  Trp  Glu  Gln  Met  Ser
    1              5                        10
```

( 2 ) INFORMATION FOR SEQ ID NO:107:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:107:

```
    Thr  Trp  Asp  Gln  Leu  Trp  Asp  Leu  Met  Lys
    1              5                        10
```

( 2 ) INFORMATION FOR SEQ ID NO:108:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:108:

Asp Ile Thr Trp Asp Gln Leu Trp Asp Leu Met
1               5                   10

( 2 ) INFORMATION FOR SEQ ID NO:109:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:109:

Asp Ile Thr Trp Asp Gln Leu Trp Asp Leu
1               5                   10

( 2 ) INFORMATION FOR SEQ ID NO:110:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:110:

Ala Glu Thr Trp Asp Gln Leu Trp His Val Met Asn Pro Ala Glu Ser
1               5                   10                  15

Gln ( 2 ) INFORMATION FOR SEQ ID NO:111:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( i x ) FEATURE:
      ( A ) NAME/KEY: Region
      ( B ) LOCATION: 2
      ( D ) OTHER INFORMATION: /note= "Xaa is selected
            from the group consisting of Asp, Glu, His, Leu, Gly,
            Ala, Gln, Thr, Ser, Tyr, Phe, Asn, Met, Arg and Ile."

( i x ) FEATURE:
      ( A ) NAME/KEY: Region
      ( B ) LOCATION: 3
      ( D ) OTHER INFORMATION: /note= "Xaa is selected
            from the group consisting of Gln, Glu, Gly, Asp, Met,
            Thr, Ala Ser, His and Asn."

( i x ) FEATURE:
      ( A ) NAME/KEY: Region
      ( B ) LOCATION: 6
      ( D ) OTHER INFORMATION: /note= "Xaa is selected
            from the group consisting of Asn Asp, Thr, Val, Glu,
            His, Ser, Gln, Ile, Lys, Arg, Leu and Lys."

( i x ) FEATURE:
      ( A ) NAME/KEY: Region
      ( B ) LOCATION: 7
      ( D ) OTHER INFORMATION: /note= "Xaa is selected
            from the group consisting of Leu, Met, Val, Ile, Phe,
            Gln, His, Nle and Ala."

( x i ) SEQUENCE DESCRIPTION: SEQ ID NO:111:

Trp Xaa Xaa Leu Trp Xaa Xaa Met (2) INFORMATION FOR SEQ ID NO:112:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (ix) FEATURE:
(A) NAME/KEY: Region
(B) LOCATION: 2
(D) OTHER INFORMATION: /note= "Xaa is selected from the group consisting of Asp, Glu, His, Leu, Gly, Ala, Gln, Thr, Ser, Tyr, Phe, Ans, Met, Arg and Ile."

(ix) FEATURE:
(A) NAME/KEY: Region
(B) LOCATION: 3
(D) OTHER INFORMATION: /note= "Xaa is selected from the group consisting of Gln, Glu, Gly, Asp, Met, Thr, Ala, Ser, His and Asn."

(ix) FEATURE:
(A) NAME/KEY: Region
(B) LOCATION: 6
(D) OTHER INFORMATION: /note= "Xaa is selected from the group consisting of Asn, Asp, Thr, Val, Glu, His, Ser, Gln, Ile, Lys, Arg, Leu and Lys."

(ix) FEATURE:
(A) NAME/KEY: Region
(B) LOCATION: 7
(D) OTHER INFORMATION: /note= "Xaa is selected from the group consisting of Leu, Met, Val, Ile, Phe, Gln, His, Nle and Ala."

(ix) FEATURE:
(A) NAME/KEY: Region
(B) LOCATION: 8
(D) OTHER INFORMATION: /note= "Xaa is norleucine."

(xi) SEQUENCE DESCRIPTION: SEQ ID NO:112:

Trp Xaa Xaa Leu Trp Xaa Xaa Xaa
1               5

PEPTIDES AND COMPOUNDS THAT BIND TO ELAM-1

CROSS-REFERENCE TO RELATED APPLICATIONS

This is a continuation of application Ser. No. 08/057,295, filed on May 5, 1993, now abandoned, which is a continuation-in-part of U.S. patent application Ser. No. 07/881,395, filed May 6, 1992, incorporated herein by reference, which is now abandoned.

BACKGROUND OF THE INVENTION

1. Field of the Invention

The present invention provides peptides and compounds that bind to endothelial leukocyte adhesion molecule 1 (ELAM-1) and methods for blocking cell adhesion. The invention has application in the fields of biochemistry and medicinal chemistry and particularly provides ELAM-1 inhibitors for use in the treatment of human disease.

2. Description of Related Art

The accumulation of blood leukocytes at sites of inflammation depends upon the localization of these leukocytes by adhesion to the vascular lining. Certain cytokines, such as interleukin 1 (IL-1) and tumor necrosis factors alpha and beta (TNF), as well as bacterial endotoxin, have been shown to act on cultured human endothelial cells to increase leukocyte adhesion. Bevilacqua et al., December 1987, *Proc. Natl. Acad. Sci. USA* 84:9238–9242, incorporated herein by reference, reports the identification of an inducible endothelial cell surface protein with a molecular weight of about 115 kD, designated "endothelial-leukocyte adhesion molecule-1" (ELAM-1, also known as LECAM-2 and E-selectin) involved in the process of leukocyte adhesion to the vascular lining. Further studies have shown that this molecule is a receptor and a member of a family of inducible receptors with related structure and function on vascular cells (see Johnston et al., 24 Mar. 1989, *Cell* 56:1033–1044).

Hession et al., 1990, *Proc. Natl. Acad. Sci. USA* 87:9238–9242, incorporated herein by reference, reports the cloning and nucleotide sequence of the ELAM-1 cDNA. The sequence shows that ELAM-1 contains an N-terminal lectin domain, followed by an epidermal growth factor like domain, a number of repeating units related to those in complement binding proteins, a transmembrane domain, and a short cytoplasmic tail. The family of adhesion molecules to which ELAM-1 belongs is known as the "selectin" family and includes the proteins GMP-140 (also known as CD62, PADGEM, P-selectin, and LECAM-3) and LAM-1 (also known as LECAM-1, MEL-14, and L-selectin). See Geng et al., 22 Feb. 1990, *Nature* 343:757–760; Springer, 2 Aug. 1990, *Nature* 346:425–434; and Bevilacqua et al., 18 Oct. 1991, *Cell* 67:233, each of which is incorporated herein by reference). Collins et al., 5 Feb. 1991*J. Biol. Chem.* 266(4):2466–2473, reports the nucleotide sequence of the ELAM-1 gene, which contains 14 exons spanning about 13 kb of DNA on chromosome 1.

The lectin motif of ELAM-1 is believed to be involved in the binding of carbohydrate ligands, and ELAM-1 has been shown to bind to sialyl-Lewis X (SLe$^x$), a terminal structure found on cell surface glycoprotein and glycolipid carbohydrate groups of neutrophils, during leukocyte adhesion (see Phillips et al., 23 Nov. 1990, *Science* 250:1130–1135; Parekh, 1991, Oxford GlycoSystems Ltd., Tech. Bull. 11; Tiemeyer et al., Feburary 1991, *Proc. Natl. Acad. Sci. USA* 88:1138–1142; and Tyrrell et al., November 1991, *Proc. Natl. Acad. Sci. USA* 88: 10372–10376, each of which is incorporated herein by reference). Other selectins, such as the leukocyte receptor CD62, also recognize the SLe$^x$ ligand (see Polley et al., July 1991, *Proc. Natl. Acad. Sci. USA* 88: 6224–6228, incorporated herein by reference). Other workers have reported the isolation of a cDNA that directs the expression of an ELAM-1 ligand. The cDNA encodes a 46 kD protein that has alpha(1,3)fucosyltransferase activity, suggesting that a fucosylated carbohydrate structure is an essential component of the ELAM-1 ligand (see Goelz et al., 21 Dec. 1990, *Cell* 63:1349–1356).

The ligands for ELAM-1 are apparently present on memory T cells, because Shimizu et al., 28 Feb. 1991, *Nature* 349:799–802, reports that ELAM-1 may be of primary importance in the initial attachment of memory T cells to inflamed endothelium in vivo and to the preferential migration of memory T cells into tissue and inflammatory sites. Picker et al., 28 Feb. 1991, *Nature* 349:796–799, reports that ELAM-1 may function as a skin vascular addressin, a tissue selective endothelial cell adhesion molecule for skin homing memory T lymphocytes. Although ELAM-1 undoubtedly serves important biological functions, the inappropriate expression of ELAM-1 can be very detrimental to the host. For instance, inappropriate production of or response to IL-1, a cytokine that also stimulates transient expression of ELAM-1, plays a role in many chronic inflammatory diseases, such as rheumatoid arthritis (RA), osteo arthritis (OA), psoriasis, inflammatory bowel disease, encephalitis, glomerulonephritis, and respiratory distress syndrome. See Bender and Lee, 1989, *Ann. Rep. Med. Chem.* 25:185–193; and U.S. Pat. No. 5,075,222, particularly columns 1 to 3, each of which is incorporated herein by reference.

By inhibiting the binding of leukocytes to ELAM-1, ELAM-1 inhibitors can be used to ameliorate the effects of inappropriate production or response to ELAM-1 or the cytokines that stimulate ELAM-1 production, such as the cytokines TNF or IL-1. Furthermore, ELAM-1 has been reported to promote tumor cell adhesion and so may be involved in cancer metastases (see Rice and Bevilacqua, 8 Dec. 1989, *Science* 246:1303–1306, incorporated herein by reference), so ELAM-1 antagonists may be beneficial in the treatment of cancer, acting to prevent metastases.

Scientists have demonstrated increased levels of ELAM-1 in (1) dermal inflammation, including Il-1-induced skin inflammation; atopic dermatitis, psoriasis, and allergic contact dermatitis; delayed-type hypersensitivity reaction induced by DNCB on human skin; and endotoxin-induced acute cutaneous inflammation in baboons; (2) intestinal inflammation, including inflamed colonic mucosa of patients with ulcerative or Crohn's colitis; inflammatory bowel disease; and intestinal graft-versus-host disease; (3) other sites of inflammation, including synovial tissues from patients with RA and OA; rat endotoxin-induced uveitis, and inflamed endothelium of asthma model (primate antigen inhalation); and (4) septic shock induced in baboons with live *E. coli*. Because ELAM-1 inhibitors can be used to inhibit the deleterious effects of inflammation, various companies have been reported to be testing such compounds for various applications. These compounds include: (1) monoclonal antibodies against ELAM-1 under testing by Otsuka; Cytel; and Biogen for treatment of acute and chronic inflammatory diseases; (2) carbohydrate inhibitors of ELAM-1 under testing by Glycomed; Cytel; and Oxford GlycoSystems/SmithKline Beecham, for inflammatory diseases and cancer; and (3) other compounds, including antisense oligonucleotides, under testing by Isis for treatment of inflammation and cancer.

The availability of cloned genes for ELAM-1, including a soluble ELAM-1 derivative, facilitates the search for agonists and antagonists of this important receptor. The availability of the recombinant receptor protein allows the study of receptor-ligand interaction in a variety of random and semi-random peptide diversity generation systems, even though the natural ligands for ELAM-1 appear to be carbohydrates. These systems include the "peptides on plasmids" system described in U.S. patent application Ser. No. 963,321 filed Oct. 15, 1992, which is a continuation-in-part of Ser. No. 778,233, filed Oct. 16, 1991, the "peptides on phage" system described in U.S. patent application Ser. No. 718, 577, filed Jun. 20, 1991, and in Cwirla et al., August 1990, Proc. Natl. Acad. Sci. USA 87:6378–6382, the "encoded synthetic library" (ESL) system described in U.S. patent application Ser. No. 946,239, filed Sep. 16, 1992, which is a continuation-in-part of Ser. No. 762,522, filed Sep. 18, 1991, and the "very large scale immobilized polymer synthesis" system described in U.S. Pat. No. 5,143,854; PCT patent publication No. 90/15070, published Dec. 13, 1990; U.S. patent application Ser. No. 624,120, filed Dec. 6, 1990; Fodor et al., 15 Feb. 1991, Science 251:767–773; Dower and Fodor, 1991, Ann. Rep. Med. Chem. 26:271–180; and U.S. patent application Ser. No. 805,727, filed Dec. 6, 1991; each of the foregoing patent applications and publications is incorporated herein by reference.

There remains a need for non-carbohydrate compounds that bind to or otherwise interact with ELAM-1 with high affinity, both for studies of the important biological activities mediated by this receptor and for treatment of disease. In similar fashion, there remains a need for compounds that bind to ELAM-1 and block the binding of leukocytes to ELAM-1. The present invention provides such compounds.

SUMMARY OF THE INVENTION

In one embodiment, the invention provides peptides and peptidomimetics that bind to ELAM-1. These compounds comprise a core structure defined by the amino acid sequence WXXLWXXM (SEQ ID NO:1), where each amino acid is indicated by standard one letter abbreviation, and X is any amino acid. Certain compounds of the invention may assume, according to computer modelling, an amphipathic helical shape, with a hydrophobic face defined by the side chains of the W, L, W, and M residues and a more hydrophilic face defined by the X residues in the core sequence.

Peptides of the invention are typically 9 or more (i.e., 12, 15, to 20) amino acids in length and comprise the 8 amino acid sequence above but can also include peptides in which the M residue is a norleucine (Nle). Preferred peptides of the invention include peptides 9 to 12 amino acid residues in length and comprising the sequence $X_1X_2X_3WX_4X_5LWX_6X_7X_8X_9$, wherein each residue can be independently selected as follows: $X_1$ is H, E, or D; $X_2$ is I, M, or Nle; $X_3$ is T or S; $X_4$ is D, E, or L; $X_5$ is Q or E; $X_6$ is N or D; $X_7$ is L, M, V, or I; $X_8$ is M or Nle; and $X_9$ is N, S, or Q. Especially preferred peptides of the invention include peptides that comprise the sequence ITWDQLWDLMK (SEQ ID NO:2), such as DITWDQLWDLMK (SEQ ID NO:3). Peptidomimetics of the invention have structures and present side chain groups similar to the preferred peptides of the invention. The present invention also provides related peptides, peptide derivatives, and peptidomimetics. The present invention also provides methods for inhibiting the binding of ELAM-1 ligands, including the ligands on leukocytes, to ELAM-1, and methods for treating disease and disease symptoms resulting from improper stimulation of ELAM-1 utilizing the compounds of the invention. The present invention further provides pharmaceutical compositions comprising one or more compounds of the invention and a physiologically acceptable carrier.

BRIEF DESCRIPTION OF THE FIGURES

FIG. 2a and 2b show the results of a cell adhesion assay in the presence of various concentrations of an ELAM-1 blocking peptide of the invention; the assay is described in Example 1.

FIG. 4 shows the $IC_{50}$ values (nM) of a variety of peptides of the invention tested in the assay shown in FIG. 3, part B. D-amino acids are preceeded by a small "D-". The SEQ. ID NOS. corresponding to the peptide sequences listed in column 1 of FIG. 4 are as follows: 3, 96, 76, 97, 10, 77, 98, 99, 84, 100, 101, 87, 102, 110, 19, 103, 104, 105, 62, 106, and 85, respectively. The SEQ. ID NOS. corresponding to the last four peptide sequences in column 3 of FIG. 4 are as follows: 2, 107, 108, and 109, respectively.

DETAILED DESCRIPTION OF THE INVENTION

I. Definitions

Figure 1:
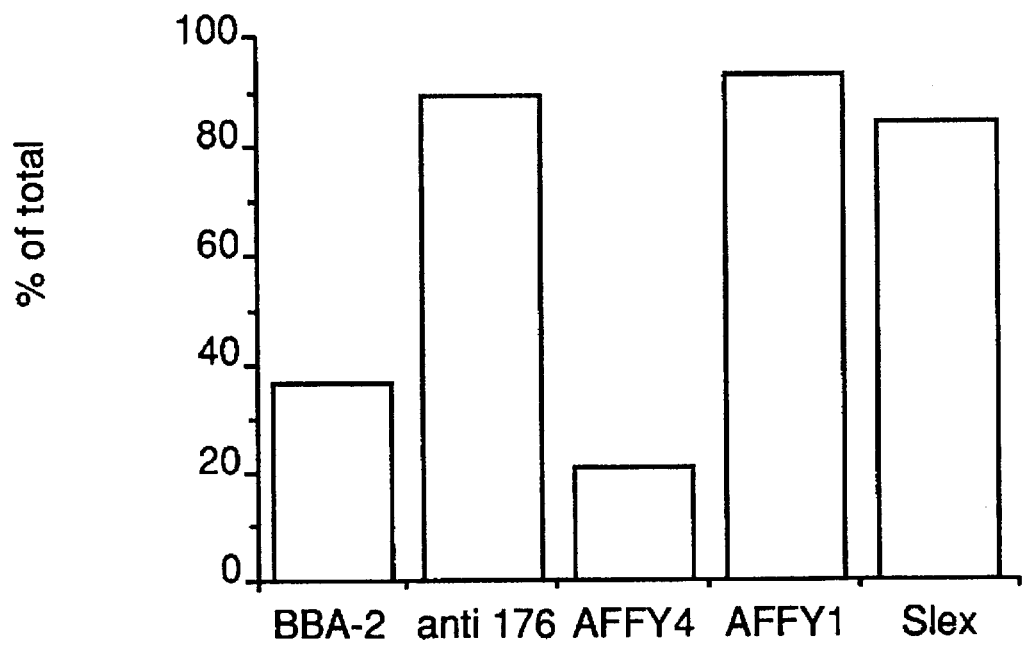
FIG. 1 shows the results of a cell adhesion assay in the presence of various compounds; the assay is described in Example 1.

To facilitate an understanding of the present invention, the following terms are defined below.

The term "pharmaceutically acceptable salts," as used herein, refers to the non-toxic alkali metal, alkaline earth metal, and ammonium salts commonly used in the pharmaceutical industry including the sodium, potassium, lithium, calcium, magnesium, barium, ammonium, and protamine zinc salts, which are prepared by methods well known in the art. The term also includes non-toxic acid addition salts, which are generally prepared by reacting the compounds of this invention with a suitable organic or inorganic acid. Representative salts include the hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, and napsylate salts, and the like.

The term "lower alkyl," as used herein, refers to straight and branched chain alkyl groups having from 1 to 6 carbon atoms, such as methyl, ethyl, n-propyl, iso-propyl, n-butyl, tert-butyl, sec-butyl, n-pentyl, n-hexyl, 1,2-dimethylbutyl, and the like. Usually, the lower alkyl group is methyl or ethyl.

The term "lower alkoxy," as used herein, refers to straight and branched chain alkoxy groups having from 1 to 6 carbon atoms, such as methoxy, ethoxy, n-propoxy, iso-propoxy, n-butoxy, tert-butoxy, sec-butoxy, n-pentoxy, n-hexoxy, 1,2-dimethylbutoxy, and the like. Usually, the lower alkoxy group is methoxy or ethoxy.

The term "lower ester derivative," as used herein, refers to straight and branched chain alkyl ester derivatives having from 1 to 6 carbon atoms, such as methyl, ethyl, n-propyl, iso-propyl, n-butyl, tert-butyl, sec-butyl, n-pentyl, n-hexyl, 1,2-dimethylbutyl ester derivatives, and the like. Usually, the lower ester derivative is a methyl ester derivative or an ethyl ester derivative.

Amino acid residues in peptides are abbreviated as follows: Phenylalanine is Phe or F; Leucine is Leu or L; Isoleucine is Ile or I; Methionine is Met or M; Norleucine is Nle; Valine is Val or V; Serine is Ser or S; Proline is Pro or P; Threonine is Thr or T; Alanine is Ala or A; Tyrosine is Tyr or Y; Histidine is His or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; Glycine is Gly or G, and X is any amino acid.

II. General Methods and Compounds of the Invention

The present invention provides compounds that bind to endothelial leukocyte adhesion molecule 1 (ELAM-1). These compounds include "lead" peptide compounds, discovered using random peptide diversity generating systems, and "derivative" compounds that have been constructed so as to have the same or similar molecular structure or shape as one or more lead compounds but that differ from the lead compound with respect to susceptibility to hydrolysis or proteolysis and/or with respect to other biological properties, such as increased affinity for ELAM-1.

The random peptide diversity generating systems employed in the discovery of the lead compounds include both the "peptides on plasmids" and "peptides on phage" systems described above. The random peptides were generally designed to be twelve or more amino acid residues in length. To generate the collection of oligonucleotides encoding the random peptides, the codon motif $(NNK)_x$, where N is nucleotide A, C, G, or T (equimolar; depending on the methodology, other nucleotides can be employed), K is G or T (equimolar), and x is 12 was used to specifiy any one of the 32 possible codons resulting from the NNK motif: 1 for each of 12 amino acids, 2 for each of 5 amino acids, 3 for each of 3 amino acids, and only one of the three stop codons. Thus, the NNK motif encodes all of the amino acids, encodes only one stop codon, and reduces codon bias.

In the systems employed, the random peptides were presented either on the surface of a phage particle, as part of a fusion protein comprising either the pIII or the pVIII coat protein of a phage fd derivative (peptides on phage), or as a fusion protein with LacI bound to a plasmid (peptides on plasmids). The phage or plasmids, including the DNA encoding the peptides, were identified and isolated by an affinity enrichment process using immobilized ELAM-1. The affinity enrichment process, sometimes called "panning," involves multiple rounds of incubating the phage or plasmids with immobilized ELAM-1, collecting the phage or plasmids that bind to ELAM-1 (along with the accompanying DNA), and producing more of the phage or plasmids (along with accompanying LacI-peptide fusion protein) collected.

Figure 3A:
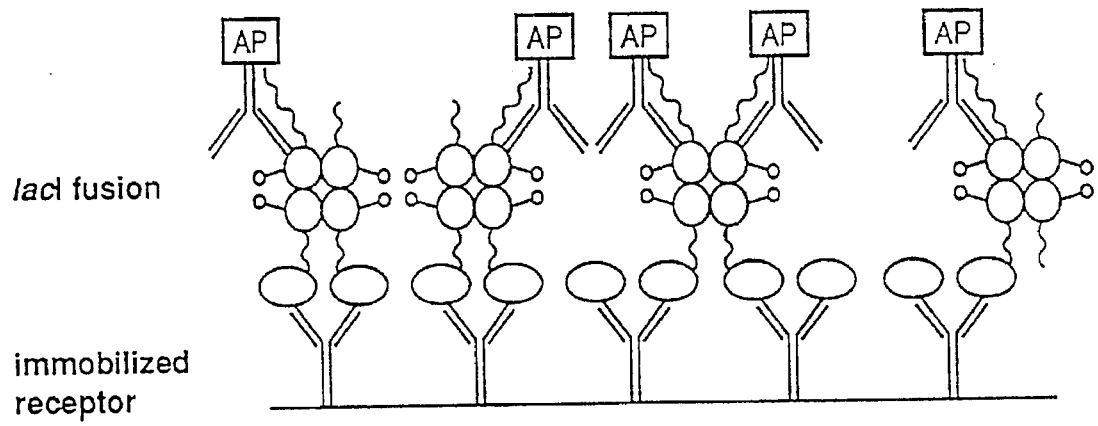
FIG. 3 shows two peptides on plasmids assay formats, in parts A and B. In part A, a binding assay is conducted in which the specificity of a peptide for immobilized ELAM-1 receptor is related to the amount of signal generated by alkaline phosphatase (AP) conjugated to anti-LacI antibodies in turn bound to LacI-peptide fusion proteins. In part B, the $IC_{50}$ of free peptides in solution is measured in a competition assay.
Figure 3B:
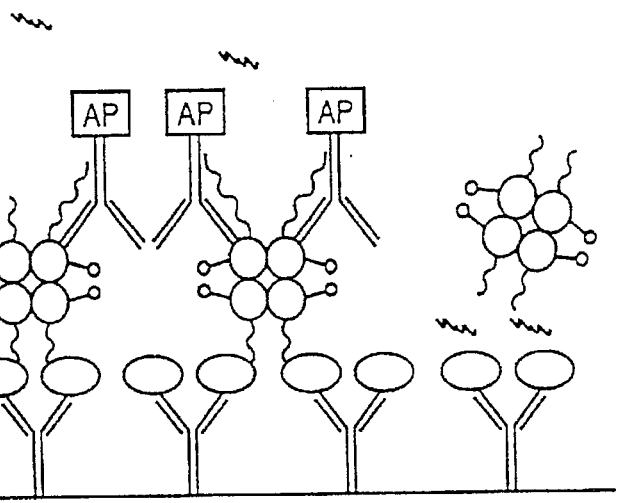

After several rounds of affinity enrichment, the phage or plasmids and accompanying peptides were examined by ELISA to determine if the peptides bind specifically to ELAM-1. This assay was carried out similarly to the procedures used in the affinity enrichment process, except that after removing unbound phage (or plasmids), the wells were typically treated with rabbit anti-phage antibody, then with alkaline phosphatase (AP)-conjugated goat anti-rabbit antibody, or with anti-LacI-AP, as shown in FIG. 3, part A, and then the amount of alkaline phosphatase in each well was determined by standard methods.

By comparing test wells with control wells (no receptor), one can determine whether a peptide binds to ELAM-1 specifically. Peptides found to bind specifically to ELAM-1 were then synthesized as the free peptide (no phage) and tested in an HL60 cell adhesion competition assay. The competition assay was carried out similarly to the ELISA, except that labeled HL60 cells were added in addition to the peptide (the control wells were typically of at least two types: (1) no immobilized ELAM-1; and (2) no peptide; see the Examples). Peptides that block the binding of labeled HL60 cells to ELAM-1 are preferred compounds of the invention.

The immobilized ELAM-1 used in the affinity enrichment and ELISA procedures was produced in recombinant host cells in a truncated form comprising the complete extracellular domain (amino acids 1 through 554). The DNA encoding ELAM-1 is commercially available (R&D Designer Genes, product code BBG57). This truncated ELAM-1 molecule can be produced in a variety of different forms and host cells. One useful form of ELAM-1 is constructed by expressing the protein as a soluble protein in baculovirus transformed host cells using standard methods; another useful form is constructed with a signal peptide for protein secretion and for glycophospholipid membrane anchor attachment. This form of anchor attachment is called "PIG-tailing;" see Caras and Weddell, 3 Mar. 1989, *Science* 243:1196–1198, and Lin et al., 10 Aug. 1990, *Science* 249:677–679, each of which is incorporated herein by reference. Using the PIG-tailing system, one can cleave the receptor from the surface of the cells expressing ELAM-1 (e.g., transformed CHO cells selected for high level expression of ELAM-1 with a cell sorter) with phospholipase C. The cleaved ELAM-1 still comprises a carboxy terminal sequence of amino acids, called the "HPAP tail," from the signal for membrane attachment and can be immobilized without further purification.

The recombinant receptor protein was immobilized by coating the wells of microtiter plates with an anti-HPAP tail antibody, blocking with bovine serum albumin (BSA) in PBS, and then binding recombinant, truncated ELAM-1 to the antibody. Using this procedure, one should perform the immobilization reaction in varying concentrations of ELAM-1 to determine the optimum amount for a given preparation, because different preparations of recombinant protein often contain different amounts of the desired protein. In addition, one should ensure that the immobilizing antibody is completely blocked (with ELAM-1 or some other blocking compound) during the affinity enrichment process. Otherwise, unblocked antibody can bind undesired phage during the affinity enrichment procedure. One can use peptides that bind to the immobilizing antibody to block unbound sites that remain after ELAM-1 immobilization to avoid this problem or one can simply immobilize the receptor directly, without the aid of an immobilizing antibody. See U.S. patent application Ser. No. 947,339, filed Sep. 18, 1992, incorporated herein by reference.

When using random peptide generation systems that allow for multivalent ligand-receptor interaction, one must recognize that the density of the immobilized receptor is an important factor in determining the affinity of the ligands that can bind to the immobilized receptor. At higher receptor densities (i.e., each anti-receptor antibody-coated well treated with 0.25 to 0.5 µg of receptor), multivalent binding is more likely to occur (if at all) than at lower receptor densities (i.e., each anti-receptor antibody-coated well treated with 0.5 to 1 ng of the receptor). If multivalent binding is occurring, then one will be more likely to isolate ligands with relatively lower affinity, unless one uses high densities of immobilized receptor to identify lead compounds and uses lower receptor densities to isolate derivative compounds with higher affinity for the receptor than the lead compounds. Using the pIII-based peptides on phage system, a 12-mer library was screened to discover a single phage that presents a lead peptide that binds to ELAM-1. The phage DNA was sequenced to determine the sequence of the peptide displayed on the surface of the phage. The peptide had the amino acid sequence: HITWDQLWNVMN (SEQ. ID NO:4). This peptide can block the adhesion of HL60 cells to immobilized ELAM-1 (see Example 1).

This peptide sequence can serve as the basis for the construction of another peptide library designed to contain a high frequency of derivatives of the peptide. Such a library can be synthesized so as to favor the production of peptides that differ from the lead peptide in only a few residues. This approach involves the synthesis of an oligonucleotide with the lead peptide coding sequence, except that rather than using pure preparations of each of the four nucleoside triphosphates in the synthesis, one uses mixtures of the four nucleoside triphosphates (i.e., 55% of the "correct" nucleotide, and 15% each of the other three nucleotides is a preferred mixture for this purpose) so as to generate derivatives of the lead peptide coding sequence.

A variety of mutagenesis strategies were used to derivatize the lead peptide by making "mutagenesis on a theme" libraries, which included mutagenesis of the original coding sequence at 70:10:10:10 and 55:15:15:15 frequencies; fixed-sliding libraries, such as HITWDQXXXXXX (SEQ ID NO:5), XXTWDQLWXXXX (SEQ ID NO:6), XXXXDQLWNVXX (SEQ ID NO:7), and XXXXXXLWNVMN (SEQ ID NO:8); an extended/mutagenized library, XXXXHITWDQLWNVMNXXXX (SEQ ID NO:9) (70:10:10:10), which was screened using standard and modified (200 μM of ELAM-1 binding peptide QITWAQLWNMMK (SEQ ID NO:10) for 2 hours, followed by glycine-HCl) elution conditions; and libraries with fixed amino acids, such as XXX-WXXLWXXMX (SEQ ID NO:11) and XXXXWXXL-WXXMXXXXXX (SEQ ID NO:12) produced in a peptides-on-plasmids system and tested under standard and low receptor density conditions. Screening such libraries yielded the ELAM-1-binding peptides shown in Tables 1–3, below.

| | |
|---|---|
| HITWDQLWNVMN (SEQ. ID NO:4) | AITWDQLWLLMS (SEQ. ID NO:46) |
| ELTWDQLWVLMS (SEQ. ID NO:13) | DVTWDQLWELMT (SEQ. ID NO:47) |
| EVTWDQLWVMMQ (SEQ. ID NO:14) | NLTWDQLWVLMS (SEQ. ID NO:48) |
| EMSWLELWNVMN (SEQ. ID NO:15) | TITWDQLWQMMS (SEQ. ID NO:49) |
| ELSWDQLWNVMN (SEQ. ID NO:16) | EMTWQELWNVMN (SEQ. ID NO:50) |
| EMTWTELWNVMN (SEQ. ID NO:17) | DMTWSQLWNVMN (SEQ. ID NO:51) |
| EMTWLGLWNVMN (SEQ. ID NO:18) | QITWMELWNLMN (SEQ. ID NO:52) |
| EITWDQLWEVMN (SEQ. ID NO:19) | EITWDQLWDVMN (SEQ. ID NO:53) |
| DISWDQLWNVMN (SEQ. ID NO:20) | QITWDQLWDLMK (SEQ. ID NO:54) |
| EMTWDQLWNVMN (SEQ. ID NO:21) | DITWDQLWNMMD (SEQ. ID NO:55) |
| DITWNMLWNMMQ (SEQ. ID NO:22) | DISWDDLWIMMN (SEQ. ID NO:56) |
| DITWHQLWNLMN (SEQ. ID NO:23) | EISWEQLWTMMN (SEQ. ID NO:57) |
| DITWEQLWNMMN (SEQ. ID NO:24) | EITWDQLWTLMT (SEQ. ID NO:58) |
| DITWHQLWNLMN (SEQ. ID NO:25) | DMTWDQLWIVMN (SEQ. ID NO:59) |
| DITWEQLWNLMN (SEQ. ID NO:26) | QITWYQLWNMMN (SEQ. ID NO:60) |
| HISWHELWNLMQ (SEQ. ID NO:27) | YITWEQLWTMMN (SEQ. ID NO:61) |
| HITWDQLWDLMQ (SEQ. ID NO:28) | QITWDQLWDLMY (SEQ. ID NO:62) |
| QITWDQLWNMMI (SEQ. ID NO:29) | QITWAQLWNMMK (SEQ. ID NO:10) |
| YITWEQLWNMMN (SEQ. ID NO:30) | HITWDQLWDIMS (SEQ. ID NO:63) |
| HITWDQLWEIMS (SEQ. ID NO:31) | HITWDQLWALMT (SEQ. ID NO:64) |
| HITWDQLWSLMS (SEQ. ID NO:32) | HITWDQLWLMMS (SEQ. ID NO:65) |
| HITWDQLWDLMQ (SEQ. ID NO:33) | HITWDQLWWIMA (SEQ. ID NO:66) |
| HITWDQLWLLMA (SEQ. ID NO:34) | HITWDQLWMLMA (SEQ. ID NO:67) |
| GSDSHITWDELWNLMNPVLA (SEQ. ID NO:35) | NWLDDITWDELWKIMNPSTA (SEQ. ID NO:68) |
| ETDDHITWDQLWRIMTATMA (SEQ. ID NO:36) | WTDTHITWDQLWHFMNMGEQ (SEQ. ID NO:69) |
| GFGEAITWDQLWDMMNGEDA (SEQ. ID NO:37) | NVAEQITWDQLWNLMSVGSS (SEQ. ID NO:70) |
| GQTGLITWDMLWNLMNPVGE (SEQ. ID NO:38) | GTGDHITWDQLWNLMINEKG (SEQ. ID NO:71) |
| EYGRHITWDQLWQLMQSATA (SEQ. ID NO:39) | MNNWHVSWEQLWDIMNGPPN (SEQ. ID NO:72) |
| ESASHITWGQLWDLMNASEV (SEQ. ID NO:40) | YWRGNITWDQLWMNIMNSEYS (SEQ. ID NO:73) |
| AGASHITWAQLMNMMNGNEG (SEQ. ID NO:41) | GSWAHITWDQLWNLMNMGTQ (SEQ. ID NO:74) |
| YGNSNITWDQLWSIMNRQTT (SEQ. ID NO:42) | AHLPHISWDTLWHIMNKGEK (SEQ. ID NO:75) |
| ESASHITWGQLWDLMNASEV (SEQ. ID NO:43) | MNNWHVSWEQLWDIMNGPPN (SEQ. ID NO:72) |
| GFGEAITWDQLWDMMNGEDA (SEQ. ID NO:44) | WTDTHITWDQLWHFMNMGEQ (SEQ. ID NO:69) |
| EMTWAELWTLME (SEQ. ID NO:45) | DYTWFELWDMMQ (SEQ. ID NO:76) |
| DYSWHDLWEMMS (SEQ. ID NO:77) | DISWRQLWDIMN (SEQ. ID NO:86) |
| EISWLGLWDIMN (SEQ. ID NO:78) | DMTWHDLWTLMS (SEQ. ID NO:87) |
| RGVWGGLWSMTW (SEQ. ID NO:79) | EMTWQQLWVVMQ (SEQ. ID NO:88) |
| AEWTWDQLWHVMNPAESQ (SEQ. ID NO:80) | RNMSWLELWEHMK (SEQ. ID NO:84) |
| SQVTWNDLWSVMNPEVVN (SEQ. ID NO:81) | HRAEWLALWEQMSP (SEQ. ID NO:89) |
| YKKEWLELWHQMQA (SEQ. ID NO:82) | RSLSWLQLWDQMK (SEQ. ID NO:90) |
| KEQQWRNLWKMMS (SEQ. ID NO:83) | KKEDWLALWRIMSVPD (SEQ. ID NO:91) |
| RNMSWLELWEHMK (SEQ. ID NO:84) | GRPTWNELWDMMQAP (SEQ. ID NO:92) |
| KRKQWIELWNIMS (SEQ. ID NO:85) | KTSEWNNLWKLMSQ (SEQ. ID NO:93) |

Examining the amino acid distribution of these peptides, one can describe the peptides as shown in Tables 2 and 3, below. In these Tables, the most frequently observed residue at each position in the conserved region is shown in the top line together with the number of peptides in which the residue was observed at that position. The other residues observed at each position are listed below the most frequently observed residue together with the number of peptides with that residue in the indicated position.

TABLE 2

Clones from Phage Libraries

| H17 | I46 | T53 | W67 | D36 | Q48 | L67 | W67 | N28 | L24 | M67 | N40 |
|-----|-----|-----|-----|-----|-----|-----|-----|-----|-----|-----|-----|
| E15 | M10 | S12 |     | E7  | E9  |     |     | D13 | M18 |     | S9  |
| D15 | L3  | V3  |     | H5  | G3  |     |     | T5  | V14 |     | Q7  |
| Q7  | V2  |     |     | L3  | D3  |     |     | V4  | I9  |     | T3  |
| N4  | Y2  |     |     | G3  | M2  |     |     | E3  | F2  |     | K2  |
| A3  | G1  |     |     | A3  | T1  |     |     | H3  |     |     | I2  |
| T1  |     |     |     |     | Q2  |     |     | S2  |     |     | D1  |
| L1  |     |     |     |     | T1  |     |     | Q2  |     |     | Y1  |
| R1  |     |     |     |     | S1  |     |     | I2  |     |     | E1  |
|     |     |     |     |     | Y1  |     |     | K1  |     |     | W1  |
|     |     |     |     |     | N1  |     |     | R1  |     |     |     |
|     |     |     |     |     | M1  |     |     | L1  |     |     |     |
|     |     |     |     |     | F1  |     |     |     |     |     |     |

TABLE 3

Clones from Peptides-on-Plasmids Libraries

| R5 | E2 | E6 | W16 | L10 | E5 | L16 | W16 | E5 | I3 | M16 | S7 |
|----|----|----|-----|-----|----|----|-----|----|----|----|----|
| K3 | A2 | S3 |     | N3  | A4 |    |     | S2 | Q3 |    | K3 |
| E2 | K2 | T3 |     | D1  | Q2 |    |     | H2 | L2 |    | Q3 |
| N2 | Q2 | Q2 |     | R1  | N2 |    |     | D2 | M2 |    | N2 |
| Q1 | M2 | D2 |     | I1  | D1 |    |     | K2 | H2 |    | D1 |
| M1 | V1 |    |     |     | S1 |    |     | R2 | V2 |    |    |
| S1 | W1 |    |     |     | H1 |    |     | N1 | A1 |    |    |
| T1 | G1 |    |     |     |    |    |     |    |    |    |    |
|    | L1 |    |     |     |    |    |     |    |    |    |    |
|    | P1 |    |     |     |    |    |     |    |    |    |    |
|    | S1 |    |     |     |    |    |     |    |    |    |    |

FIG. 4 shows the $IC_{50}$ values for various peptides of the invention, which were produced synthetically as free peptides, as measured in assays conducted as shown in FIG. 3, part B. The Lac-I peptide fusion protein used in all assays was DQITWAQLWNMMKGGTVE (SEQ ID NO: 94). As shown in the Figure, a number of the peptides have $IC_{50}$ values in the low (1–10) nanomolar range. The norleucine derivatives, in which the conserved M is replaced with Nle, are especially noteworthy, as these derivatives may be more stable under certain enviromental conditions than other peptides of the invention that contain an M at this position.

A lead peptide sequence also provides a means to determine the minimum size of an ELAM-1 binding, cell adhesion blocking compound of the invention. Several deletion analogs of a lead peptide of the invention are shown in FIG. 4; one preferred peptide is ITWDQLWDLMK (SEQ ID NO:2). Using the "very large scale immobilized polymer synthesis" system described in U.S. Pat. No. 5,143,845 and related publications, supra, one not only can determine the minimum size of a peptide with ELAM-1 binding activity, but also can make all of the peptides that form the group of peptides that differ from the lead compound in one, two, or more residues, or that differ in containing non-natural amino acids. This collection of peptides and peptidomimetics can then be screened for ability to bind to ELAM-1. This immobilized polymer synthesis system or other peptide synthesis methods, such as the ESL method discussed above, can also be used to synthesize every truncation, deletion, and every combination of truncation and deletion analogs of the peptide compounds of the invention.

As noted above, the peptides of the invention have also been prepared by classical methods known in the art by using standard solid phase techniques. The standard methods include exclusive solid phase synthesis, partial solid phase synthesis, fragment condensation, classical solution synthesis, and recombinant DNA technology. See, e.g., Merrifield, 1963, *J. Am. Chem. Soc. 85:2149*, incorporated herein by reference. On solid phase, the synthesis is typically commenced from the C-terminal end of the peptide using an α-amino protected resin. A suitable starting material can be prepared, for instance, by attaching the required α-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky et al., 1966, *Chem. Ind.* (London) 38:1597. The benzhydrylamine (BHA) resin has been described by Pietta and Marshall, 1970, *Chem. Commn.* 650, and is commercially available from Beckman Instruments, Inc., Palo Alto, Calif., in the hydrochloride form.

Thus, the compounds of the invention can be prepared by coupling an α-amino protected amino acid to the chloromethylated resin with the aid of, for example, cesium bicarbonate catalyst, according to the method described by Gisin, 1973, *Helv. Chim. Acta* 56:1467. After the initial coupling, the α-amino protecting group is removed by a choice of reagents including trifluoroacetic acid (TFA) or hydrochloric acid (HCl) solutions in organic solvents at room temperature. The α-amino protecting groups are those known to be useful in the art of stepwise synthesis of peptides. Included are acyl type protecting groups (e.g. formyl, trifluoroacetyl, acetyl), aromatic urethane type protecting groups (e.g. benzyloxycarboyl (Cbz) and substituted Cbz), aliphatic urethane protecting groups (e.g. t-butyloxycarbonyl (Boc), isopropyloxycarbonyl, cyclohexyloxycarbonyl) and alkyl type protecting groups (e.g. benzyl, triphenylmethyl). Boc is a preferred protecting group. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

The side chain protecting groups for Tyr include tetrahydropyranyl, tert-butyl, trityl, benzyl, Cbz, Z-Br-Cbz, and 2,5-dichlorobenzyl. The side chain protecting groups for Asp include benzyl, 2,6-dichlorobenzyl, methyl, ethyl, and cyclohexyl. The side chain protecting groups for Thr and Ser include acetyl, benzoyl, trityl, tetrahydropyranyl, benzyl, 2,6-dichlorobenzyl, and Cbz. The side chain protecting groups for Thr and Ser is benzyl. The side chain protecting groups for Arg include nitro, tosyl (Tos), Cbz, adamantyloxycarbonyl mesitoylsulfonyl (Mts), or Boc. The side chain protecting groups for Lys include Cbz, 2-chlorobenzyloxycarbonyl (2-Cl-Cbz), 2-bromobenzyloxycarbonyl (2-BrCbz), Tos, or Boc. After removal of the α-amino protecting group, the remaining protected amino acids are coupled stepwise in the desired order. Each protected amino acid is generally reacted in about a 3-fold excess using an appropriate carboxyl group activator such as dicyclohexylcarbodiimide (DCC) in solution, for example, in methylene chloride ($CH_2Cl_2$), dimethyl formamide (DMF) mixtures.

After the desired amino acid sequence has been completed, the desired peptide is decoupled from the resin support by treatment with a reagent such as hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the ususal fashion by treatment with hydrogen fluoride to give the free amides, alkylamides, or dialkylamides.

In preparing the esters of the invention, the resins used to prepare the peptide acids are employed, and the side chain protected peptide is cleaved with base and the appropriate alcohol, i.e., methanol. Side chain protecting groups are then removed in the usual fashion by treatment with hydrogen fluoride to obtain the desired ester. These solid phase peptide synthesis procedures are well known in the art and further described in Stewart, *Solid Phase Peptide Syntheses* (Freeman and Co., San Francisco, 1969).

These procedures can also be used to synthesize peptides in which amino acids other than the 20 naturally occurring, genetically encoded amino acids are substituted at one, two, or more positions of any of the compounds of the invention. For instance, naphthylalanine can be substituted for tryptophan, facilitating synthesis. Other synthetic amino acids that can be substituted into the peptides of the present invention include L-hydroxypropyl, L-3,4-dihydroxyphenylalanyl, α-amino acids such as L-α-hydroxylysyl and D-α-methylalanyl, L-α-methylalanyl, β amino acids, and isoquinoly. D amino acids and non-naturally occurring synthetic amino acids can also be incorporated into the peptides of the present invention.

One can also modify the amino and/or carboxy terminus of the peptide compounds of the invention to produce other compounds of the invention. Amino terminus modifications include methylating (i.e., —$NHCH_3$ or —$NH(CH_3)_2$), acetylating, adding a carbobenzoyl group, or blocking the amino terminus with any blocking group containing a carboxylate functionality defined by RCOO—, where R is selected from the group consisting of naphthyl, acridinyl, steroidyl, and similar groups. Carboxy terminus modifications include replacing the free acid with a carboxamide group or forming a cyclic lactam at the carboxy terminus to introduce structural constraints. One can also cyclize the peptides of the invention, or incorporate a desamino or descarboxy residue at the termini of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof. One can replace the naturally occurring side chains of the 20 genetically encoded amino acids (or any L or D amino acid) with other side chains, for instance with groups such as alkyl, lower alkyl, cyclic 4-, 5-, 6-, to 7-membered alkyl, amide, amide lower alkyl, amide di(lower alkyl), lower alkoxy, hydroxy, carboxy and the lower ester derivatives thereof, and with 4-, 5-, 6-, to 7-membered hetereocyclic. In particular, proline analogs in which the ring size of the proline residue is changed from 5 members to 4, 6, or 7 members can be employed. Cyclic groups can be saturated or unsaturated, and if unsaturated, can be aromatic or non-aromatic. Heterocyclic groups preferably contain one or more nitrogen, oxygen, and/or sulphur heteroatoms. Examples of such groups include the furazanyl, furyl, imidazolidinyl, imidazolyl, imidazolinyl, isothiazolyl, isoxazolyl, morpholinyl (e.g. morpholino), oxazolyl, piperazinyl (e.g. 1-piperazinyl), piperidyl (e.g. 1-piperidyl, piperidino), pyranyl, pyrazinyl, pyrazolidinyl, pyrazolinyl, pyrazolyl, pyridazinyl, pyridyl, pyrimidinyl, pyrrolidinyl (e.g. 1-pyrrolidinyl), pyrrolinyl, pyrrolyl, thiadiazolyl, thiazolyl, thienyl, thiomorpholinyl (e.g. thiomorpholino), and triazolyl. These heterocyclic groups can be substituted or unsubstituted. Where a group is substituted, the substituent can be alkyl, alkoxy, halogen, oxygen, or substituted or unsubstituted phenyl.

One can also readily modify peptides by phosphorylation, and other methods for making peptide derivatives of the compounds of the present invention are described in Hruby et al., 1 Jun. 1990, *Biochem J.* 268(2):249–262, incorporated herein by reference. Thus, the peptide compounds of the invention also serve as structural models for non-peptidic compounds with similar biological activity. Those of skill in the art recognize that a variety of techniques are available for constructing compounds with the same or similar desired biological activity as the lead peptide compound but with more favorable activity than the lead with respect to solubility, stability, and susceptibility to hydrolysis and proteolysis. See Morgan and Gainor, 1989, *Ann. Rep. Med. Chem.* 24:243–252, incorporated herein by reference. These techniques include replacing the peptide backbone with a backbone composed of phosphonates, amidates, carbamates, sulfonamides, secondary amines, and N-methylamino acids.

The compounds of the invention are useful in vitro as unique tools for understanding the biological role of ELAM-1, as well as other receptors of the selectin family, such as CD62, that may bind to the peptide compounds of the invention. The compounds of the invention can also be used to evaluate the many factors thought to influence, and be influenced by, the cell adhesion process. The present compounds are also useful in the development of other compounds that bind to ELAM-1, because the present compounds provide important SAR information that facilitate that development.

The compounds of the invention can also be administered to warm blooded animals, including humans, to block the adhesion of leukocytes to cells expressing ELAM-1 in vivo. Thus, the present invention encompasses methods for therapeutic treatment of ELAM-1 related disorders that comprise administering a compound of the invention in amounts sufficient to block the adhesion of leukocytes to ELAM-1 in vivo. For example, the peptides and compounds of the invention can be administered to treat symptoms related to the overproduction of cytokines that stimulate expression of ELAM-1, or other members of the selectin family. Accordingly, the present invention includes pharmaceutical compositions comprising, as an active ingredient, at least one of the peptides or other compounds of the invention in association with a pharmaceutical carrier or diluent. The compounds of the invention can be administered by oral, parenteral (intramuscular, intraperitoneal, intravenous (IV) or subcutaneous injection), transdermal, nasal, vaginal, rectal, or sublingual routes of administration and can be formulated in dosage forms appropriate for each route of administration.

Solid dosage forms for oral administration include capsules, tablets, pills, powders, and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration include pharmaceutically acceptable emulsions, solutions, suspensions, syrups, with the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment desired. Generally dosage levels of between 0.001 to 10 mg/kg of body weight daily are administered to mammals to obtain effective ELAM-1 blocking activity.

As can be appreciated from the disclosure above, the present invention has a wide variety of applications. Accordingly, the following examples are offered by way of illustration, not by way of limitation.

EXAMPLE 1

HL60 Cell Adhesion Assay

This example describes the results of a cell adhesion assay in which the ability of HL60 cells (a promyelocytic leukemia-60 cell clone that expresses Sle$^x$ and is available from the ATCC) to adhere to immobilized ELAM-1 was tested in the presence of various compounds, including the ELAM-1 blocking peptide of the invention.

The assay requires HL60 cells labeled with tritiated thymidine. To label the cells, about 10 million HL60 cells are collected by centrifugation (2500 RPM for 3 minutes) and resuspended in 15 mL of DMEM/F12 plus 5% fetal calf serum containing 2 µCi/mL of tritiated thymidine (Amersham). The cells are then placed in a T75 flask and incubated at 37° C. for 24 hours. The cells are then collected by centrifugation, washed twice with RPMI/HEPES/0.1% FCS, and resuspended in the same solution at a concentration of about one to two million cells per mL. About 100 µL of this cell preparation are used per well of a 96-well microtiter dish in the assay.

The wells of the microtiter dish were first coated with the anti-receptor immobilizing antibody, an anti-HPAP-tail antibody, using about 2.5 µg of antibody per well. The wells were then treated with a solution composed of 1% BSA in PBS and then with a 1:10 dilution (1:100 and 1:500 dilutions and immobilizations were also conducted and tested) of a soluble ELAM-1 harvest (the ELAM-1 harvest, prepared by treating cells expressing PIG-tailed ELAM-1 with phospholipase C and collecting the resulting solution, was diluted in a solution composed of RPMI, HEPES, 0.1% BSA, and 0.1% sodium azide). All compounds tested were added prior to the addition of the labeled HL60 cells and allowed to incubate at 4° C. for one hour.

After the test compound incubation period, 100 µL of labeled HL60 cells were added to each well, and the microtiter plate was incubated at 4° C. for 30 minutes. Then, the wells were washed three times with RPMI 1640 plus 0.1% FCS using a multichannel pipettor. After the wells were washed, 100 µL of 0.1N NaOH were added to each well, and the microtiter plate was incubated at room temperature for 10 minutes. After this incubation, aliquots were removed from each well and placed in scintillation vials; scintillation fluid was added to each vial; and the radioactivity in each aliquot was quantitated by LS counting.

The compounds tested were as follows: (1) "BBA-2" is an ELAM-1 blocking antibody purchased from R&D Systems and used at a concentration of about 200 nM; (2) "anti 176" is an antibody that does not bind to the ELAM-1 used at a concentration of about 200 nM as a negative control; (3) "AFFY 4" is peptide HITWDQLWNVMN (SEQ ID NO:4), with a free amino and a free carboxy terminus, used at a concentration of 200 µM after dissolving in DMSO and diluting in PBS/DMSO to a final concentration of 5% DMSO; (4) "AFFY 1" is an unrelated peptide used at a concentration of about 200 µM as a negative control; and (5) a "SLe$^x$" derivative, monofucosyl monosialyllactose at a concentration of about 200 µM. The results of the assay are presented in FIG. 1, which reflects HL60 cell binding as a percent of the binding observed in the absence of any added compound.

As shown in FIG. 1, the peptide HITWDQLWNVMN (SEQ ID NO:4) blocked over 80% of the cell binding that occurred in the absence of added compound. This result compares favorably with the blocking observed in the presence of BBA-2 (about 65%). The negative controls (anti 176 and AFFY 1) showed no significant blocking of HL60 binding. Although SLe$^x$ did not exhibit significant blocking of cell adhesion at the concentration used in this assay, subsequent experiments showed that SLe$^x$ does block cell adhesion if used at a concentration of 500 to 1000 µM.

The peptide HITWDQLWNVMN (SEQ ID NO:4) was tested in the cell adhesion assay at varying concentrations (from 0.5 to 100 μM) along with a negative control (the AFFY 1 peptide). The results of this assay, plotted as cpm observed against peptide concentration, are shown in FIG. 2a and FIG. 2b. The results show that the peptide HIT-WDQLWNVMN (SEQ ID NO:4) can inhibit binding of HL60 cells by about 50% in this assay at a concentration of 50 μM. These results demonstrate that the peptide can be used to block cells from binding to ELAM-1.

Figure 5:
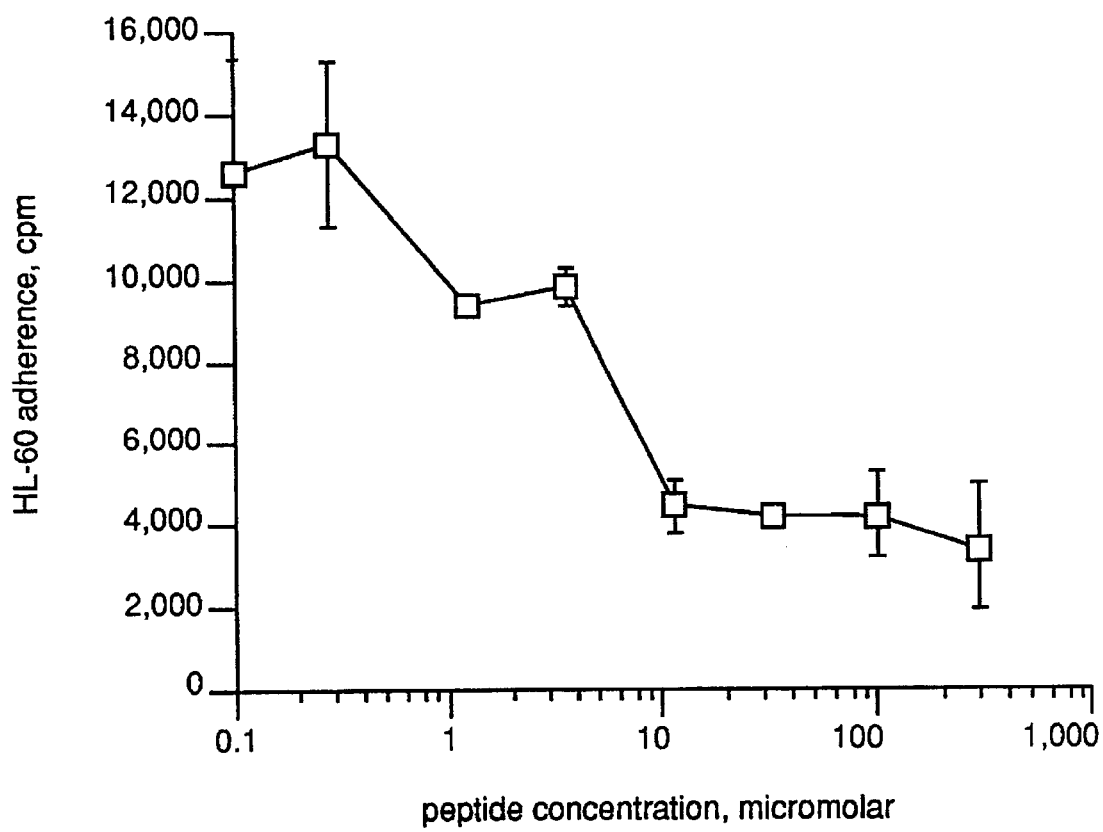
FIG. 5 shows the results of a cell adhesion assay in the presence of a preferred peptide of the invention, DITWDQLWDLMK (SEQ ID NO:3).

FIGS. 3 and 4 show two assay formats for peptides of the invention and the results of an assay in which the $IC_{50}$ of a variety of peptides of the invention is determined (see FIG. 4). FIG. 5 shows the results of a cell adhesion assay conducted with peptide DITWDQLWDLMK (SEQ ID NO:3). The peptide exhibits the desired inhibition of cell adhesion.

Although the foregoing invention has been described in some detail by way of illustration and example for purposes of clarity and understanding, it will be apparent that certain changes and modifications may be practiced within the scope of the appended claims.

---

We claim:

1. A peptide that binds ELAM-1 and which comprises an amino acid sequence $X_1X_2X_3WX_4X_5LWX_6X_7X_8X_9$ (SEQ ID NO: 113), wherein each residue can be independently selected as follows: $X_1$ is H, E, or D; $X_2$ is I, M or Nle; $X_3$ is T or S; $X_4$ is D, E, or L; $X_5$ is Q or E; $X_6$ is N or D; $X_7$ is L, M, V, or I; $X_8$ is M or Nle; and $X_9$ is N, S or Q.

2. A peptide comprising a sequence of amino acids: DITWDQLWDLMK (SEQ ID NO:3).

3. A peptide comprising a sequence of amino acids: DGDITWDQLWDLMK (SEQ ID NO:96).

4. A peptide comprising a sequence of amino acids: DYTWFELWDMMQ (SEQ ID NO:76).

5. A peptide comprising a sequence of amino acids: DITWDELWKIMN (SEQ ID NO:97).

6. A peptide comprising a sequence of amino acids: QITWAQLWNMMK (SEQ ID NO:10).

7. A peptide comprising a sequence of amino acids: DYSWHDLWEMMS (SEQ ID NO:77).

8. A peptide comprising a sequence of amino acids: DITWDQLWDLNleK (SEQ ID NO:98).

9. A peptide comprising a sequence of amino acids: HITWDQLWRIMT (SEQ ID NO:99).

10. A peptide comprising a sequence of amino acids: d-DITWDQLWDLMK, wherein d- indicates a D-amino acid.

11. A peptide comprising a sequence of amino acids: Dd-ITWDQLWDLMK, wherein d- indicates a D-amino acid.

12. A peptide comprising a sequence of amino acids: DITWDQLWDLMK-CONH$_2$, wherein—CONH$_2$ represents an amidated carboxy terminus.

13. A peptide comprising a sequence of amino acids: ITWDQLWDLMK (SEQ ID NO:2).

14. A peptide comprising a sequence of amino acids: HITWDQLWNVMN (SEQ ID NO:4).

* * * * *